(12) United States Patent
Fujimori et al.

(10) Patent No.: US 6,329,409 B1
(45) Date of Patent: Dec. 11, 2001

(54) AMINE DERIVATIVES AND SKIN PREPARATIONS FOR EXTERNAL USE CONTAINING THE SAME

(75) Inventors: Taketoshi Fujimori; Yukihiro Ohashi; Kazuhiko Higuchi; Junko Ishikawa; Takashi Kitahara, all of Tochigi (JP)

(73) Assignee: KAO Corporation, Tokyo (JP)

( * ) Notice: Subject to any disclaimer, the term of this patent is extended or adjusted under 35 U.S.C. 154(b) by 0 days.

(21) Appl. No.: 09/786,358

(22) PCT Filed: Sep. 21, 1999

(86) PCT No.: PCT/JP99/05141

§ 371 Date: Mar. 14, 2001

§ 102(e) Date: Mar. 14, 2001

(87) PCT Pub. No.: WO00/17152

PCT Pub. Date: Mar. 30, 2000

(30) Foreign Application Priority Data

Sep. 21, 1998 (JP) .................................................. 10-266400

(51) Int. Cl.[7] ........................ C07C 217/28; A01K 31/495
(52) U.S. Cl. ......................... 514/376; 424/401; 548/232; 564/507
(58) Field of Search ........................... 564/507; 548/232; 514/376

(56) References Cited

U.S. PATENT DOCUMENTS 4,609,659   9/1986   Hartman ............................................

FOREIGN PATENT DOCUMENTS

WO 91/14688   10/1991   (WO) .................................................

OTHER PUBLICATIONS

W. R. Roush, et al., J. Org. Chem., vol. 50, No. 20, pp. 3752–3757, "Directed Openings of 2,3–Epoxy Alcohols Via Reactions With Isocyanates: Synthesis of (+)–Erythro–Dihydrosphingosine", 1985.

A. Bongini, et al., J. Chem. Soc. Perkin Trans. 1, No. 5, pp. 935–939, "A New Approach To (±)–2–Amino–2–Deoxytetritol Derivatives", 1985.

S. W. McCombie, et al., Tetrahedron Letters, vol. 28, No. 45, pp. 5395–5398, "Cyclofunctionalisation Reactions of Epoxyalcohol Derivatives. 3. Cyclisation–Acyl Migration of N–Benzoylcarbamates to Stereodefined Oxazolidinones. A New, Diasterospecific Route to Thiamphenicol", 1987.

G. Cardillo, et al., J. Org. Chem., vol. 51, No. 5, pp. 713–717, "Oxazolidin–2–Ones From Allylic Amines by Means of Iodine and Carbonate Anion on Polymeric Support. A Convenient Synthesis of (±)–Propranolol", 1986.

*Primary Examiner*—Robert Gerstl
(74) *Attorney, Agent, or Firm*—Oblon, Spivak, McClelland, Maier & Neustadt, P.C.

(57) ABSTRACT

The invention relates to an amine derivative represented by the general formula (1):

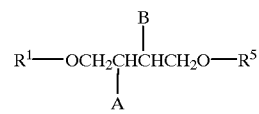

wherein $R^1$ is a $C_1$–$C_{30}$ hydrocarbon group which may be interrupted by an ether linkage, with the proviso that phenyl and benzyl groups are excluded; one of A and B is

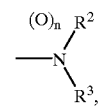

and the other of them is —$OR^4$; $R^2$ and $R^3$ are individually H, amidino group, alkanoyl group, $C_1$–$C_{20}$ hydrocarbon group, or the like; $R^4$ and $R^5$ are individually H, phosphoryl group, or the like, and an external skin care composition containing the same. The external skin care composition exhibits excellent preventing effects on aging of the skin, etc.

13 Claims, 3 Drawing Sheets

AMINE DERIVATIVES AND SKIN PREPARATIONS FOR EXTERNAL USE CONTAINING THE SAME

TECHNICAL FIELD

The present invention relates to an amine derivative which has excellent preventing effects (wrinkle preventing and improving effect, pigmentation preventing and improving effect, etc.) on aging of the skin, and improving effects (keratonosis improving effect, pimple preventing and improving effect, etc.) on cutaneous aberration caused by abnormal keratinization, and an external skin care composition containing such an amine derivative.

BACKGROUND ART

In the skin, balance between cell growth and keraninization is destroyed by external irritation such as ultraviolet rays, aging, etc., and so its healthy formation is prevented to induce pachymenia and keratonosis.

As a method for preventing and improving cutaneous aberration, it has heretofore been conducted to apply a moisturizer, blood circulation accelerator or pigmentation preventing agent to the skin. However, the homeostasis that a living body possesses has not been sufficiently improved.

Various compositions and methods have been proposed for preventing or removing wrinkles (Japanese Patent Application Laid-Open Nos. 185005/1987, WO 94/21595, etc.). However, it has been desired to develop compounds which exhibit far excellent effects.

It is accordingly an object of the present invention to provide a novel compound having excellent effects of preventing the occurrence of wrinkles and removing the wrinkles, preventing and improving pigmentation, improving keratinization, and preventing and improving pimple, and the like, and an external skin care composition containing such a compound.

DISCLOSURE OF THE INVENTION

According to the present invention, there is provided an amine derivative represented by the general formula (1):

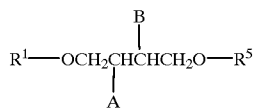

wherein $R^1$ is a hydrocarbon group having 1 to 30 carbon atoms, which may be interrupted by an ether linkage, with the proviso that phenyl and benzyl groups are excluded;

one of A and B is

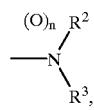

and the other of them is $—OR^4$;

$R^2$ and $R^3$ are the same or different from each other and are individually a hydrogen atom, an amidino group, an alkanoyl group or a hydrocarbon group having 1 to 20 carbon atoms, which may have 1 to 3 substituent groups selected from hydroxyl, alkoxy and carboxyl groups, or $R^2$ and $R^3$ may form a 5- or 6-membered nitrogen-containing heterocycle together with the adjacent nitrogen atom, or $R^3$ and $R^4$, or $R^3$ and $R^5$ may be bonded to each other through a carbonyl group to form an oxazolidone ring;

$R^4$ and $R^5$ are the same or different from each other and are individually a hydrogen atom or a phosphoryl group, or $R^4$ or $R^5$ may form the oxazolidone ring together with $R^3$; and n is a number of 0 or 1, or a quaternary ammonium salt or acid-addition salt thereof.

According to the present invention, there is also provided an external skin care composition comprising the amine derivative represented by the general formula (1), or a quaternary ammonium salt or acid-addition salt thereof.

The compound according to the present invention has a structural feature that the oxygen atom is present adjacently to $R^1$ in the general formula (1). When the external skin care composition comprising the compound (1) is used, aging of the skin is prevented (prevention and improvement of wrinkles, prevention and improvement of pigmentation, etc.), cutaneous troubles caused by abnormal keratinization are improvement (improvement of keratinization, prevention and improvement of pimple).

BEST MODE FOR CARRYING OUT THE INVENTION

Figure 1:
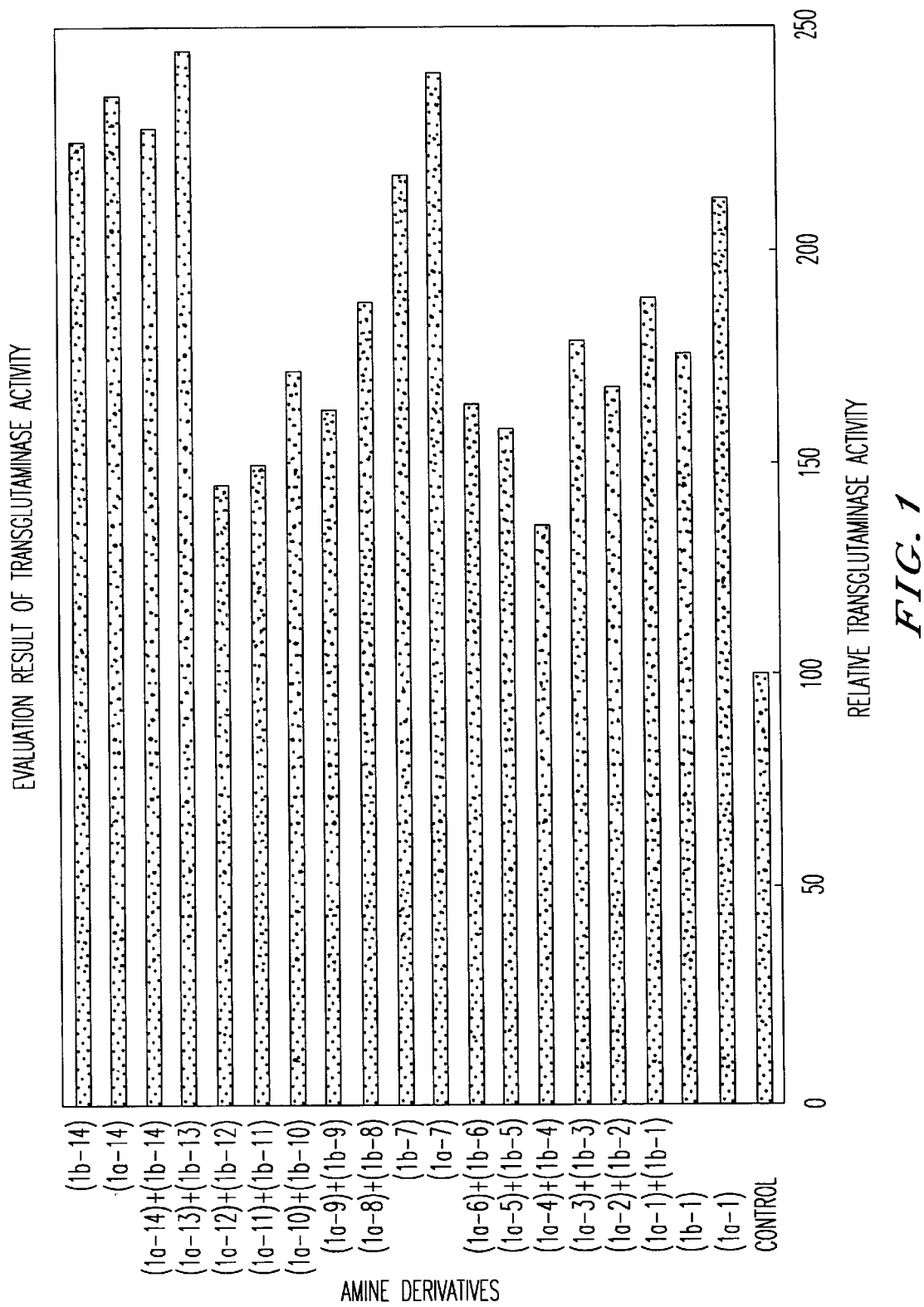
FIGS. 1 and 2 illustrate transglutaminase activities upon addition of the amine derivatives (1) according to the present invention.

Compounds, in which $R^1$ in the general formula (1) is a benzyl group, are described in J. Chem. Soc. Perkin Trans., 1(5), 935–939 (1985). However, this literature does not mention anything about fields in which the compounds, in which $R^1$ is a benzyl group, can be utilized.

On the other hand, WO 94/21595 describes the fact that various amine derivatives are useful for external skin care compositions. However, the compounds represented by the general formula (1) are not specifically shown.

In the general formula (1), the hydrocarbon group having 1 to 30 carbon atoms, which may be interrupted by an ether linkage, is preferably a hydrocarbon group having 8 to 30 carbon atoms, which may be interrupted by an ether linkage, more preferably an alkyl or alkenyl group having 8 to 30 carbon atoms, which may be interrupted by an ether linkage, particularly preferably an alkyl group having 8 to 30 carbon atom or an alkoxyalkyl group having 8 to 30 carbon atoms. Said hydrocarbon group includes linear, branched and cyclic hydrocarbon groups, with a linear or branched hydrocarbon group being preferred.

Particularly preferable examples of $R^1$ include an n-octyl group, an n-decyl group, an n-dodecyl group, an n-tridecyl group, an n-tetradecyl group, an n-hexadecyl group, an n-octadecyl group, a 12-methylhexadecyl group, isostearyl groups such as a methylheptadecyl group, a 12-methoxyoctadecyl group, a 9-(2-methylhexyloxy)nonyl group, 9-(2-ethylhexyloxy)nonyl group, and a 9-(3,5,5-trimethyl-hexyloxy)nonyl group.

One of A and B is

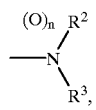

and the other of them is —OR⁴.

Accordingly, the compounds of the general formula (1) are divided into the following formulae (1a) and (1b).

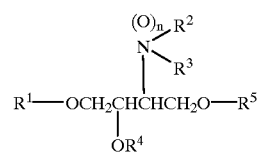 (1a)

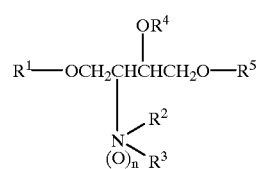 (1b)

wherein $R^1$ to $R^5$ have the same meanings as defined above.

The hydrocarbon groups represented by $R^2$ and $R^3$ and having 1 to 20 carbon atoms are preferably linear, branched or cyclic hydrocarbon groups having 1 to 12 carbon atoms, particularly preferably alkyl groups having 1 to 8 carbon atoms or aralkyl groups having 7 to 12 carbon atoms. Specific examples of the hydrocarbon groups include methyl, ethyl, n-propyl, isopropyl, n-butyl, n-hexyl and benzyl groups. These hydrocarbon groups may have 1 to 3 (preferably 1 or 2) substituent groups selected from hydroxyl, alkoxy and carboxyl groups. As the alkoxy groups among these substituent groups, are preferred alkoxy groups having 1 to 8 carbon atoms, with methoxy and ethoxy groups being particularly preferred.

As the alkanoyl groups represented by $R^2$ and $R^3$, are preferred alkanoyl groups having 1 to 8 carbon atoms, with an acetyl group being particularly preferred.

Examples of the 5- or 6-membered heterocycle formed by $R^2$ and $R^3$ together with the adjacent nitrogen atom include pyrrolidine and piperazine, with pyrrolidine being particularly preferred.

The oxazolidone ring formed by bonding $R^3$ and $R^4$ or $R^4$ and $R^5$ to each other through a carbonyl group is a 2-oxazolidone ring.

$R^4$ and $R^5$ are preferably hydrogen atoms, and n is a number of 0 or 1, with 0 being preferred.

Typical examples of the amine derivatives (1) are shown in the following Tables 1 to 6.

TABLE 1

(1a)

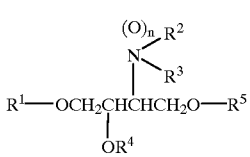

| Compound No. | $R^1$ | $R^2$ | $R^3$ | $R^4$ | $R^5$ | n |
|---|---|---|---|---|---|---|
| 1a-1 | n-$C_{13}H_{27}$ | $CH_3$ | $CH_3$ | H | H | 0 |
| 1a-2 | iso-$C_{18}H_{37}$ | $CH_3$ | $CH_3$ | H | H | 0 |
| 1a-3 | 12-Me-$C_{16}H_{33}$ | $CH_3$ | $CH_3$ | H | H | 0 |
| 1a-4 | n-$C_8H_{17}$ | $CH_3$ | $CH_3$ | H | H | 0 |
| 1a-5 | n-$C_{12}H_{25}$ | $CH_3$ | $CH_3$ | H | H | 0 |
| 1a-6 | n-$C_{14}H_{29}$ | $CH_3$ | $CH_3$ | H | H | 0 |
| 1a-7 | n-$C_{13}H_{27}$ | $CH_3$ | H | H | H | 0 |
| 1a-8 | n-$C_{13}H_{27}$ | Benzyl | H | H | H | 0 |
| 1a-9 | n-$C_{13}H_{27}$ | —$(CH_2)_2OH$ | H | H | H | 0 |
| 1a-10 | n-$C_{13}H_{27}$ | —$(CH_2)_3OMe$ | H | H | H | 0 |
| 1a-11 | n-$C_{13}H_{27}$ | n-$C_4H_9$ | H | H | H | 0 |
| 1a-12 | n-$C_{13}H_{27}$ | n-$C_{14}H_{29}$ | H | H | H | 0 |
| 1a-13 | n-$C_{13}H_{27}$ | Pyrrolidine | ($R^2 + R^3$) | H | H | 0 |
| 1a-14 | n-$C_{14}H_{29}$ | $CH_3$ | H | H | H | 0 |

TABLE 2

(1a)

| Compound No. | $R^1$ | $R^2$ | $R^3$ | $R^4$ | $R^5$ | n |
|---|---|---|---|---|---|---|
| 1a-15 | n-$C_8H_{17}$ | Pyrrolidine | ($R^2 + R^3$) | H | H | 0 |
| 1a-16 | n-$C_{10}H_{21}$ | Pyrrolidine | ($R^2 + R^3$) | H | H | 0 |
| 1a-17 | n-$C_{12}H_{25}$ | Pyrrolidine | ($R^2 + R^3$) | H | H | 0 |
| 1a-18 | n-$C_{14}H_{29}$ | Pyrrolidine | ($R^2 + R^3$) | H | H | 0 |
| 1a-19 | n-$C_{16}H_{33}$ | Pyrrolidine | ($R^2 + R^3$) | H | H | 0 |
| 1a-20 | 12-Methoxystearyl | $CH_3$ | $CH_3$ | H | H | 0 |
| 1a-21 | 3,5,5-Trimethyl-hexyloxynonyl | $CH_3$ | $CH_3$ | H | H | 0 |
| 1a-22 | 2-Ethylhexyloxy-nonyl | $CH_3$ | $CH_3$ | H | H | 0 |
| 1a-23 | 2-Methylhexyloxy-nonyl | $CH_3$ | $CH_3$ | H | H | 0 |
| 1a-24 | 12-Methoxystearyl | $CH_3$ | H | H | H | 0 |
| 1a-25 | 3,5,5-Trimethyl-hexyloxynonyl | $CH_3$ | H | H | H | 0 |
| 1a-26 | 2-Ethylhexyloxy-nonyl | $CH_3$ | H | H | H | 0 |
| 1a-27 | n-$C_{13}H_{27}$ | —$CH_2CO_2H$ | H | H | H | 0 |
| 1a-28 | n-$C_{13}H_{27}$ | $NH_2$ — C(=NH)— | H | H | H | 0 |
| 1a-29 | n-$C_{13}H_{27}$ | $CH_3$ | $CH_3$ | H | H | 1 |

TABLE 3

(1a)

| Compound No. | $R^1$ | $R^2$ | $R^3$ | $R^4$ | $R^5$ | n |
|---|---|---|---|---|---|---|
| 1a-30 | n-$C_{13}H_{27}$ | $CH_3$ | 2-Oxazolidone ($R^3 + R^5$), $R^4$ = H | | | 0 |

TABLE 3-continued

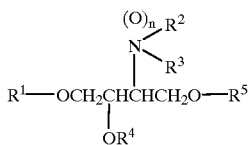

(1a)

| Compound No. | R¹ | R² | R³ | R⁴ | R⁵ | n |
|---|---|---|---|---|---|---|
| 1a-31 | n-C₁₃H₂₇ | —COCH₃ | CH₃ | H | H | 0 |
| 1a-32 (Succinate) | n-C₁₃H₂₇ | CH₃ | H | H | H | 0 |
| 1a-33 | n-C₁₃H₂₇ | CH₃ | CH₃ | H | —PO₃H₂ | 0 |
| 1a-34 | n-C₁₃H₂₇ | H | H | H | H | 0 |
| 1a-35 | n-C₁₆H₃₃ | CH₃ | CH₃ | H | H | 0 |
| 1a-36 | n-C₁₆H₃₃ | CH₃ | H | H | H | 0 |
| 1a-37 | n-C₁₂H₂₅ | CH₃ | H | H | H | 0 |
| 1a-38 | iso-C₁₈H₃₇ | CH₃ | H | H | H | 0 |
| 1a-39 | 12-Me-C₁₆H₃₃ | CH₃ | H | H | H | 0 |
| 1a-40 | n-C₁₀H₂₃ | CH₃ | CH₃ | H | H | 0 |
| 1a-41 | n-C₁₃H₂₇ | —(CH₂)₂OMe | H | H | H | 0 |
| 1a-42 | n-C₁₃H₂₇ | CH₂OH<br>—CHCO₂H | H | H | H | 0 |

TABLE 4

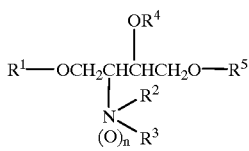

(1b)

| Compound No. | R¹ | R² | R³ | R⁴ | R⁵ | n |
|---|---|---|---|---|---|---|
| 1b-1 | n-C₁₃H₂₇ | CH₃ | CH₃ | H | H | 0 |
| 1b-2 | iso-C₁₈H₃₇ | CH₃ | CH₃ | H | H | 0 |
| 1b-3 | 12-Me-C₁₆H₃₃ | CH₃ | CH₃ | H | H | 0 |
| 1b-4 | n-C₈H₁₇ | CH₃ | CH₃ | H | H | 0 |
| 1b-5 | n-C₁₂H₂₅ | CH₃ | CH₃ | H | H | 0 |
| 1b-6 | n-C₁₄H₂₉ | CH₃ | CH₃ | H | H | 0 |
| 1b-7 | n-C₁₃H₂₇ | CH₃ | H | H | H | 0 |
| 1b-8 | n-C₁₃H₂₇ | Benzyl | H | H | H | 0 |
| 1b-9 | n-C₁₃H₂₇ | —(CH₂)₂OH | H | H | H | 0 |
| 1b-10 | n-C₁₃H₂₇ | —(CH₂)₃OMe | H | H | H | 0 |
| 1b-11 | n-C₁₃H₂₇ | n-C₄H₉ | H | H | H | 0 |
| 1b-12 | n-C₁₃H₂₇ | n-C₁₄H₂₉ | H | H | H | 0 |
| 1b-13 | n-C₁₃H₂₇ | Pyrrolidine | (R² + R³) | H | H | 0 |
| 1b-14 | n-C₁₄H₂₉ | CH₃ | H | H | H | 0 |
| 1b-15 | n-C₈H₁₇ | Pyrrolidine | (R² + R³) | H | H | 0 |
| 1b-16 | n-C₁₀H₂₁ | Pyrrolidine | (R² + R³) | H | H | 0 |
| 1b-17 | n-C₁₂H₂₅ | Pyrrolidine | (R² + R³) | H | H | 0 |
| 1b-18 | n-C₁₄H₂₉ | Pyrrolidine | (R² + R³) | H | H | 0 |

TABLE 5

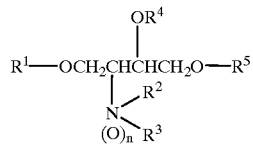

(1b)

| Compound No. | R¹ | R² | R³ | R⁴ | R⁵ | n |
|---|---|---|---|---|---|---|
| 1b-19 | n-C₁₆H₃₃ | Pyrrolidine | (R² + R³) | H | H | 0 |
| 1b-20 | 12-Methoxystearyl | CH₃ | CH₃ | H | H | 0 |
| 1b-21 | 3,5,5,-Trimethyl-hexyloxynonyl | CH₃ | CH₃ | H | H | 0 |
| 1b-22 | 2-Ethylhexyloxynonyl | CH₃ | CH₃ | H | H | 0 |
| 1b-23 | 2-Methylhexyloxynonyl | CH₃ | CH₃ | H | H | 0 |
| 1b-24 | 12-Methoxystearyl | CH₃ | H | H | H | 0 |
| 1b-25 | 3,5,5-Trimethyl-hexyloxynonyl | CH₃ | H | H | H | 0 |
| 1b-26 | 2-Ethylhexyloxynonyl | CH₃ | H | H | H | 0 |
| 1b-27 | n-C₁₃H₂₇ | —CH₂CO₂H | H | H | H | 0 |
| 1b-28 | n-C₁₃H₂₇ |  | H | H | H | 0 |
| 1b-29 | n-C₁₃H₂₇ | CH₃ | CH₃ | H | H | 1 |
| 1b-30 | n-C₁₃H₂₇ | CH₃ | 2-Oxazolidone (R³ + R⁵), R⁴ = H | | | 0 |
| 1b-31 | n-C₁₃H₂₇ | —COCH₃ | CH₃ | H | H | 0 |
| 1b-32 (Succinate) | n-C₁₃H₂₇ | CH₃ | H | H | H | 0 |

TABLE 6

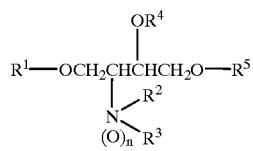

(1b)

| Compound No. | R¹ | R² | R³ | R⁴ | R⁵ | n |
|---|---|---|---|---|---|---|
| 1b-33 | n-C₁₃H₂₇ | CH₃ | CH₃ | H | —PO₃H₂ | 0 |
| 1b-34 | n-C₁₃H₂₇ | H | H | H | H | 0 |
| 1b-35 | n-C₁₆H₃₃ | CH₃ | CH₃ | H | H | 0 |
| 1b-36 | n-C₁₆H₃₃ | CH₃ | H | H | H | 0 |
| 1b-37 | n-C₁₂H₂₅ | CH₃ | H | H | H | 0 |
| 1b-38 | iso-C₁₈H₃₇ | CH₃ | H | H | H | 0 |
| 1b-39 | 12-Me-C₁₆H₃₃ | CH₃ | H | H | H | 0 |
| 1b-40 | n-C₁₀H₂₃ | CH₃ | CH₃ | H | H | 0 |
| 1b-41 | n-C₁₃H₂₇ | —(CH₂)₂OMe | H | H | H | 0 |
| 1b-42 | n-C₁₃H₂₇ | CH₂OH<br>—CHCO₂H | H | H | H | 0 |

As the quaternary ammonium salt of the amine derivative (1), is preferred a quaternary ammonium salt obtained by reacting the amine derivative (1) with an alkyl halide. As the alkyl halide, is preferred an alkyl halide having 1 to 4 carbon atoms, with methyl chloride or methyl bromide being particularly preferred.

The configuration of the amine derivative (1) according to the present invention may be any of a D-threo form, L-threo form, D-erythro form and L-erythro form. When the amine derivative (1) is used for an external skin care composition, these configurational isomers may be used either singly or in any combination thereof.

Examples of the acid-addition salt of the amine derivative (1) include mineral acid salts such as a hydrochloride, sulfate and phosphate, and organic acid salts such as a succinate, lactate, fumarate, glycolate, citrate, hexadecanoate, octadecanoate, tartrate and benzoate. Among these, the hydrochloride, succinate, lactate and glycolate are preferred.

The amine derivative (1) according to the present invention can be prepared in accordance with, for example, the following preparation process 1 or preparation process 2.

(Preparation Process 1)

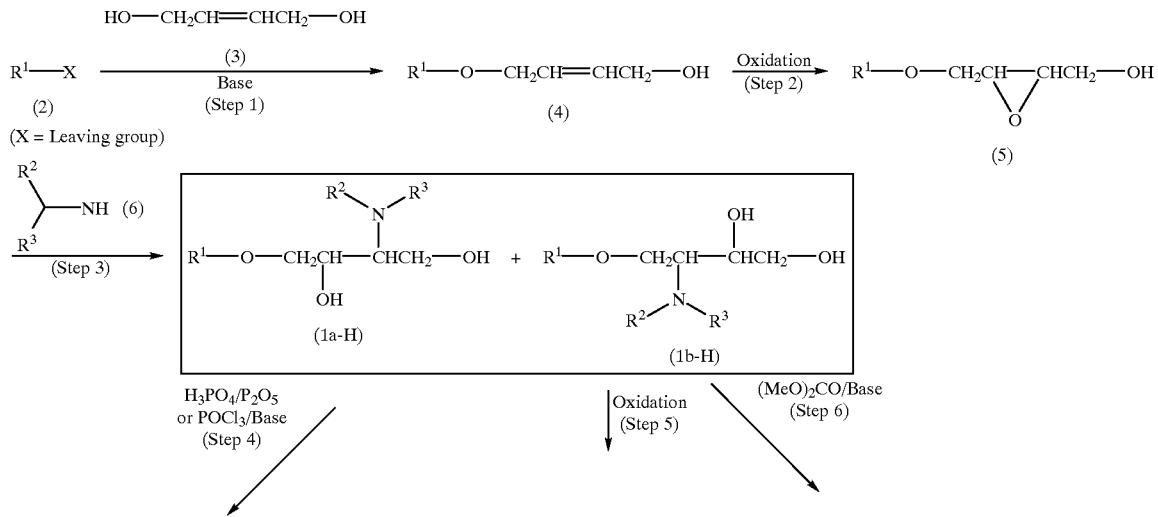

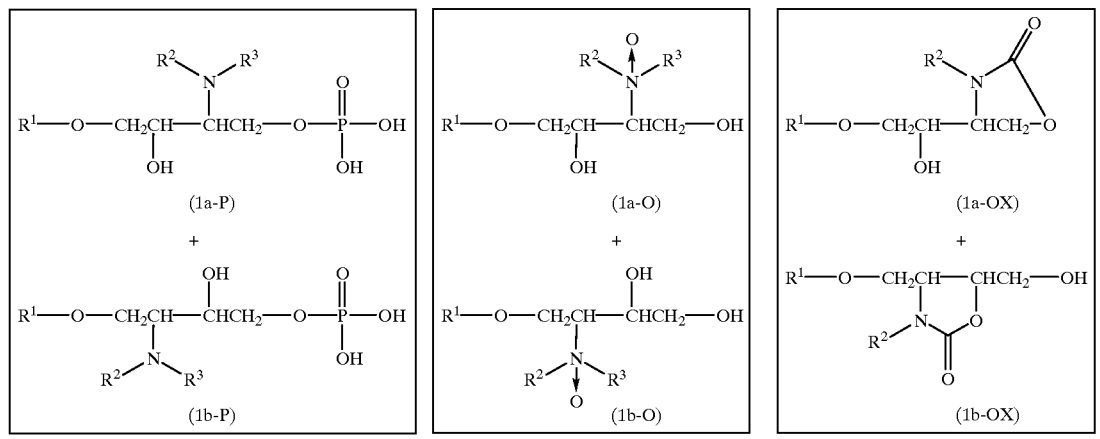

(Preparation Process 2)

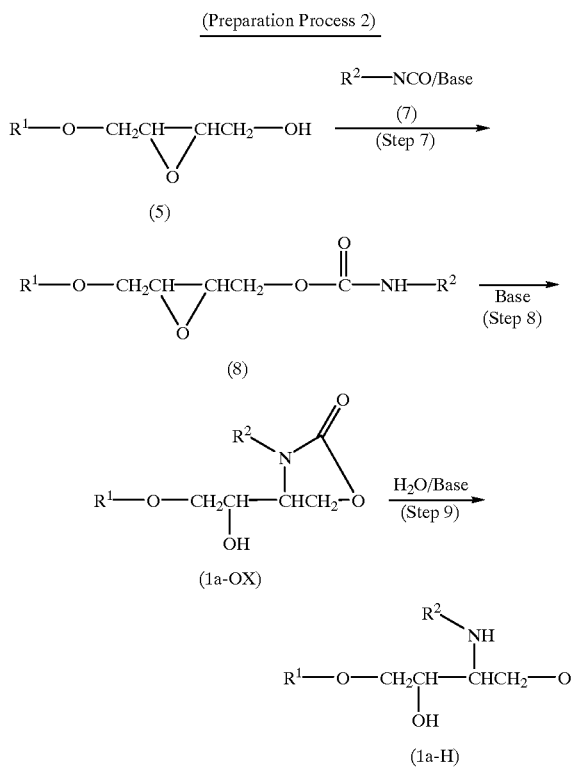

wherein X is a leaving group such as a halogen atom or methanesulfonyl group, and $R^1$ and $R^2$ have the same meaning as defined above.

The respective steps of the above-described reaction schemes will hereinafter be described.

<Step 1>

Butenediol (3) is mixed with a base such as potassium hydroxide, sodium hydroxide or sodium hydride, a compound (4) is added to this mixture to conduct a reaction, thereby obtaining a compound (4). The reaction may be conducted either without using any solvent or in the presence of a solvent such as toluene, xylene, tetrahydrofuran, N,N-dimethylformamide or t-butyl alcohol.

<Step 2>

The compound (4) is reacted with an oxidizing agent such as m-chloroperbenzoic acid, peracetic acid, hydrogen peroxide or t-butyl hydroperoxide, thereby obtaining an oxirane derivative (5). As a catalyst, may be used a catalyst such as tetraisopropyl orthotitanate, tungstic acid, sodium tungstate or molybdic acid. As a phase-transfer catalyst, may be used a quaternary ammonium salt such as tetrabutylammonium bromide, tetrabutylammonium hydrogensulfate, trioctylmethylammonium chloride, trioctylmethylammonium hydrogensulfate or lauryltrimethyl-ammonium chloride. As a pH adjustor, may be used sodium hydroxide, sodium acetate, sodium dihydrogenphosphate, disodium hydrogenphosphate or the like. The reaction may be conducted either without using any solvent or in the presence of a solvent such as methylene chloride, toluene, xylene, hexane, water or alcohol.

<Step 3>

The oxirane derivative (5) is reacted with an amine (6), thereby obtaining amine derivatives (1a-H) and (1b-H). As a catalyst, may be used tetraisopropyl orthotitanate or the like. The reaction may be conducted either without using any solvent or in the presence of a solvent such as methylene chloride, tetrahydrofuran, water or alcohol. The mixture thus obtained may be or may not be separated into the respective compounds. The separation may be conducted in accordance with a method known per se in the art, such as column chromatography on silica gel.

<Step 4>

The amine derivative (1a-H) or (1b-H) is reacted with a phosphorylating agent such as pyrophosphoric acid, phosphoric acid, diphosphorus pentaoxide or phosphorus oxychloride, thereby obtaining a phosphate derivative (1a-P) or (1b-P). The mixture of the amine derivatives (1a-H) and (1b-H) may be reacted. Examples of the base include pyridine, dimethylaminopyridine and triethylamine.

<Step 5>

The amine derivative (1a-H) or (1b-H) is reacted with an oxidizing agent such as m-chloroperbenzoic acid, peracetic acid, hydrogen peroxide or t-butyl hydroperoxide, thereby obtaining N-oxide derivatives (1a-O) and (1b-O). As a catalyst, may be used a catalyst such as tungstic acid or molybdic acid. The reaction may be conducted either without using any solvent or in the presence of a solvent such as water or alcohol.

<Step 6>

The amine derivative (1a-H) or (1b-H) is reacted with dimethyl carbonate in the presence of a base such as sodium hydride, potassium hydroxide or sodium hydroxide, thereby obtaining carbamate derivatives (1a-OX) and (1b-OX).

<Step 7>

The oxirane derivative (5) is reacted with an isocyanate derivative (7) such as methyl isocyanate, benzyl isocyanate or octadecyl isocyanate in the presence of a base such as triethylamine, pyridine or sodium hydroxide, thereby obtaining a compound (8). The reaction may be conducted either without using any solvent or in the presence of a solvent such as methylene chloride, tetrahydrofuran or toluene.

<Step 8>

A base such as sodium hydroxide, potassium hydroxide or sodium hydride is caused to act on the compound (8), whereby a carbamate derivative (1a-OX) can be synthesized. As a solvent, is used a solvent inert to the reaction, such as tetrahydrofuran or toluene.

<Step 8>

The compound (1a-OX) is hydrolyzed in the presence of a base such as sodium hydroxide, lithium hydroxide or potassium hydroxide, thereby obtaining an amine derivative (1a-H).

The amine derivatives (1) thus obtained have effects on various cutaneous symptoms caused by aging of the skin and keratonosis, for example, wrinkle preventing and improving effect, pigmentation preventing and improving effect, keratonosis improving effect, pimple preventing and improving effect, etc., and are useful for external skin care compositions for medicines and cosmetics.

The external skin care composition according to the present invention may be used in various forms such as medicinal external skin care compositions such as ointments, external skin care compositions and cosmetic compositions such as emulsified cosmetics, creams, emulsions, cosmetic lotions, oily cosmetics, lip sticks, foundations, skin cleansing compositions, hair tonics, hair styling compositions, hair grooming compositions and hair growth stimulants. The external skin care composition according to the present invention can be prepared by incorporating those ingredients generally employed in such forms, such as oily substances such as vegetable oil and animal oil, analgesic and antiphlogistic agents, analgesics, disinfectants, astringents, emollients, hormones, vitamins, moisturizers, ultraviolet absorbents, alcohols, chelating agents, pH adjustors, preservatives, thickeners, coloring matter and perfume bases, into the amine derivative (1) in accordance with a method known per se in the art.

The amount of the amine derivative (1) incorporated into the external skin care composition is preferably 0.0001 to 10% by weight (hereinafter indicated merely by "%"), particularly preferably 0.001 to 1%. The external skin care composition according to the present invention is used by applying it in a proper amount to the skin in accordance with a method known per se in the art.

EXAMPLES

Synthesis Example 1

Synthesis (Synthetic Process A) of Compound (1a-1) and Compound (1b-1):

(1) Synthesis of 2,3-epoxy-4-tridecyloxy-1-butanol:

A flask was charged with sodium hydride (19.2 g, 50 mmol) and N,N-dimethylformamide (75 g) in a nitrogen atmosphere, to which butenediol (75.3 g, 0.86 mol) was added under ice cooling. The resultant mixture was then heated to 60° C., and an alkyl halide (1-bromotridecane (76 g, 28.9 mmol)) was added dropwise over 2 hours. Under the same conditions, the resultant mixture was stirred for 1 hour and then cooled to room temperature, to which water was added to conduct extraction with n-hexane. The resultant organic layer was washed with saturated saline, dried over anhydrous magnesium sulfate and then filtered. The resultant filtrate was concentrated under reduced pressure and then distilled under reduced pressure to obtain 4-tridecyloxy-2-buten-1-ol (64.4 g, 82%).

A flask was charged with the thus-obtained 4-tridecyloxy-2-buten-1-ol (5.0 g, 18.5 mmol) and methylene chloride (25 ml), to which m-chloroperbenzoic acid (5.5 g, 1.2 eq.) was added under ice cooling. The resultant mixture was then stirred at room temperature for 4 hours. An aqueous solution of sodium thiosulfate was added, extraction was conducted with chloroform, and the resultant organic layer was dried over anhydrous magnesium sulfate and then filtered. The resultant filtrate was purified by column chromatography on basic alumina and silica gel to obtain the title compound.

$^1$H-NMR (CDCl$_3$, δ):

0.80–0.95(m,3H), 1.12–1.78(m,22H), 3.15–3.32(m,2H), 3.37–3.90(m,6H). m.p.: 74.2–73.1° C.

(2) Synthesis of a mixture of Compound (1a-1) and Compound (1b-1):

An autoclave was charged with 2,3-epoxy-4-tridecyl-oxy-1-butanol (4.0 g, 14.0 mmol) and amine (40% aqueous solution of dimethylamine, 0.14 mol), and the resultant mixture was stirred at 100° C. for 2 hours. The reaction mixture was then cooled to room temperature and transferred to a flask to concentrate it under reduced pressure. The resultant residue was purified by column chromatography on silica gel to obtain the title compound (3.7 g, 80%).

$^1$H-NMR (CDCl$_3$, δ):

0.80–0.98(m,3H), 1.15–1.75(m,22H), 2.35–2.80(m,7H), 3.32–3.88(m,9H). IR (cm$^{-1}$):

3432, 2928, 2860, 1466, 1406, 1116, 1047.

(3) Separation of Compound (1a-1) and Compound (1b-1):

The mixture obtained in the above step was separated by means of.HPLC (separation conditions: column YMC-Pack ODS 500×20 mm I.D. 5 μm, eluent methanol: 90 mmol/L aqueous solution of ammonium acetate 90:10). Compound (1a-1):

$^1$H-NMR (CDCl$_3$, δ):

0.88(t,J=6.7Hz,3H), 1.11–1.62(m,22H), 2.10(brs,2H), 2.36(s,3H), 2.60–2.80(m,1H), 3.33–3.58(m,6H), 3.62–3.88(m,1H). Compound (1b-1):

$^1$H-NMR (CDCl$_3$, δ):

0.88(t,J=6.7Hz,3H), 1.18–1.68(m,22H), 2.40(s,3H), 2.45–2.58(m,1H), 2.72(brs,2H), 3.38–3.80(m,7H). IR (cm$^{-1}$):

3428, 2932, 2860, 1464, 1120.

Synthesis Examples 2 to 9

Compounds of the present invention shown in Tables 7 to 10 were synthesized by respectively using their corresponding alkyl halides and amines shown in Tables 7 to 10 in accordance with Synthetic Process (A).

TABLE 7

| Syn. Ex | Invention compound | NMR* | IR (cm$^{-1}$) | Alkyl halide | Amine |
|---|---|---|---|---|---|
| 2 | Mixture of (1a-2) and (1b-2) | 0.75–0.98(m, 6H) 1.02–1.76(m, 29H), 2.00–2.80(m, 9H), 3.32–3.90(m, 7H). | 3432, 2928, 2860, 1460, 1408, 1120. | Isostearyl bromide | 40% Aqueous sol. of dimethylamine |
| 3 | Mixture of (1a-3) and (1b-3) | 0.75–0.94(m, 6H), 0.96–1.65(m, 27H), 2.44(s, 6H), 2.50–2.90(m, 1H), 3.32–4.02(m, 9H). $^{13}$C-NMR(CDCl$_3$, δ) 14.1, 19.8, 23.1, 26.0, 26.2, 27.1, 29.2–30.1, 32.8, 36.8, 37.2, 41.3, 41.6, 57.7, 64.2, 64.7, 66.4, 68.1, 69.0, 69.2, 71.6, 72.1, 73.0. | | 1-Bromo-12-methyl-hexadecane | 40% Aqueous sol. of dimethylamine |
| 4 | Mixture of (1a-4) and (1b-4) | 0.87(t, J=6.4Hz, 3H), 1.10–1.70(m, 12H), 2.38(s, 3H), 2.37(s, 3H), 2.40–2.80(m, 1H), 3.30–3.90(m, 9H). | 3432, 2932, 2860, 1462, 1112, 1044. | 1-Bromooctane | 40% Aqueous sol. of dimethylamine |
| 5 | Mixture of (1a-5) and (1b-5) | 0.88(t, J=6.7Hz, 3H), 1.10–1.75(m, 20H), 2.36(s, 3H), 2.38(s, 3H), 2.40–2.80(m, 1H), 3.30–3.90(m, 9H) | | 1-Bromododecane | 40% Aqueous sol. of dimethylamine |

TABLE 7-continued

| Syn. Ex | Invention compound | NMR* | IR (cm$^{-1}$) | Alkyl halide | Amine |
|---|---|---|---|---|---|
| 6 | Mixture of (1a-6) and (1b-6) | 0.88(t, J=6.7Hz, 3H), 1.10–1.75(m, 24H), 2.36(s, 3H), 2.38(s, 3H), 2.40–2.80(m, 1H), 3.30–3.90(m, 9H) | | 1-Bromotetradecane | 40% Aqueous sol. of dimethylamine |

*Indicating $^1$H-NMR (CDCl$_3$, δ) unless expressly noted.

TABLE 8

| Syn. Ex | Invention compound | NMR* | IR (cm$^{-1}$) | Alkyl halide | Amine |
|---|---|---|---|---|---|
| 7 | (1a-7) | 0.88(t, J=6.7Hz, 3H), 1.10–1.72(m, 22H), 2.12(brs, 3H), 2.48(s, 3H), 2.62–2.76(m, 1H), 3.34–3.90(m, 7H). | 3332, 2932, 2860, 1470, 1116. | 1-Bromotridecane | 40% Aqueous sol. of methylamine |
| 7 | (1b-7) | 0.88(t, J=6.7Hz, 3H), 1.06–1.70(m, 22H), 2.24(brs, 3H), 2.48(s, 3H), 2.40–2.60(m, 1H), 3.38–3.82(m, 7H). | 3328, 2932, 2860, 1470, 1108. | 1-Bromotridecane | 40% Aqueous sol. of methylamine |
| 8 | Mixture of (1a-8) and (1b-8) | 0.80–0.98(m, 3H), 1.15–1.72(m, 22H), 2.50(brs, 3H), 2.62–2.90(m, 1H), 3.35–4.01(m, 9H), 7.20–7.40(m, 5H). | 3348, 2924, 2856, 1490, 1470, 1118, 1094, 1052. | 1-Bromotridecane | Benzylamine |
| 9 | Mixture of (1a-9) and (1b-9) | 0.72–0.95(m, 3H), 1.05–1.70(m, 22H), 2.50–3.85(m, 16H). | 3348, 2928, 2860, 1468, 1108, 1062. | 1-Bromotridecane | Ethanolamine |
| 10 | Mixture of (1a-10) and (1b-10) | 0.88(t, J=6.7Hz, 3H), 1.05–1.88(m, 24H), 2.35(brs, 3H), 2.55–3.00(m, 3H), 3.34(s, 3H), 3.40–3.88(m, 9H). | 3428, 2928, 2860, 1466, 1120. | 1-Bromotridecane | 3-Methoxy-1-propylamine |
| 11 | Mixture of (1a-11) and (1b-11) | 0.80–1.02(m, 6H), 1.10–1.75(m, 26H), 2.45–2.90(m, 6H), 3.35–3.85(m, 7H). | 3336, 2932, 2860, 1468, 1112. | 1-Bromotridecane | n-Butylamine |
| 12 | Mixture of (1a-12) and (1b-12) | 0.78–0.98(m, 6H), 1.15–2.05(m, 49H), 2.40–2.85(m, 3H), 3.32–3.86(m, 7H). | 3412, 2960, 2924, 2856, 1470, 1112. | 1-Bromotridecane | n-Tetradecylamine |

*Indicating $^1$H-NMR (CDCl$_3$, δ) unless expressly noted.

TABLE 9

| Syn. Ex | Invention compound | NMR* | IR (cm$^{-1}$) | Alkyl halide | Amine |
|---|---|---|---|---|---|
| 13 | Mixture of (1a-13) and (1b-13) | 0.88(t, J=6.7Hz, 3H), 1.12–1.70(m, 28H), 2.48–2.95(m, 7H), 3.32–3.90(m, 7H). | 3420, 2932, 2860, 1470, 1106. | 1-Bromotridecane | 80% Ethanol of pyrrolidine |
| 14 | Mixture of (1a-14) and (1b-14) | 0.86(t, J=6.7Hz, 3H), 1.05–1.65(m, 24H), 2.44(s, 3H), 2.45–2.72(m, 1H), 2.98(brs, 3H), 3.35–3.85(m, 7H). | 3336, 2928, 2856, 1470, 1122. | 1-Bromotridecane | 40% Aqueous sol. of methylamine |
| 14 | (1a-14) | 0.85(t, J=6.7Hz, 3H), 1.06–1.32(m, 24H), 2.46(s, 3H), 2.52(ddd, J=6.7, 4.2, 3.4Hz, 1H), 2.82(brs, 3H), 3.44–3.50(m, 2H), 3.53(d, J=5.2Hz, 2H), 3.57(dd, J=11.6, 3.4Hz, 1H), 3.73(dd, J=11.6, 4.2Hz, 1H), 3.76(dt, J=6.7, 5.2Hz, 1H). | — | 1-Bromotridecane | 40% Aqueous sol. of methylamine |
| 14 | (1b-14) | 0.85(t, J=6.7Hz, 3H), 1.06–1.32(m, 24H), 2.46(s, 3H), 2.69(ddd, J=5.2, 4.8, 4.0Hz, 1H), 3.00(brs, 3H), 3.41–3.46(m, 2H), 3.48(dd, J=9.8, 4.0Hz, 1H), 3.61(dd, J=9.8, 4.8Hz, 1H), 3.66(ddd, J=5.2, 3.7, 3.7Hz, 1H), 3.71(dd, J=11.3, 3.7Hz, 1H), 3.79(dd, J=11.3, 3.7Hz, 1H). | — | 1-Bromotridecane | 40% Aqueous sol. of methylamine |

*Indicating $^1$H-NMR (CDCl$_3$, δ) unless expressly noted.

TABLE 10

| Syn. Ex | Invention compound | NMR* | IR (cm$^{-1}$) | Alkyl halide | Amine |
|---|---|---|---|---|---|
| 15 | Mixture of (1a-15) and (1b-15) | 0.88(t, J=6.7Hz, 3H), 1.10–1.95(m, 18H), 2.52–3.02(m, 5H), 3.25–3.90(m, 7H). | 3424, 2932, 2860, 1466, 1110. | 1-Bromooctane | 80% Ethanol sol. of pyrrolidine |
| 16 | Mixture of (1a-16) and (1b-16) | 0.88(t, J=6.7Hz, 3H), 1.10–1.90(m, 22H), 2.52–3.02(m, 5H), 3.30–3.90(m, 7H). | 3424, 2932, 2860, 1468, 1112. | 1-Bromodecane | 80% Ethanol sol. of pyrrolidine |
| 17 | Mixture of (1a-17) and (1b-17) | 0.88(t, J=6.7Hz, 3H), 1.12–1.88(m, 26H), 2.56–3.02(m, 5H), 3.32–3.88(m, 7H). | 3424, 2928, 2860, 1464, 1108. | 1-Bromododecane | 80% Ethanol sol. of pyrrolidine |
| 18 | Mixture of (1a-18) and (1b-18) | 0.88(t, J=6.7Hz, 3H), 1.12–1.70(m, 28H), 2.48–2.95(m, 7H), 3.32–3.90(m, 7H). | 3420, 2932, 2860, 1470, 1106. | 1-Bromotetradecane | 80% Ethanol sol. of pyrrolidine |
| 19 | Mixture of (1a-19) and (1b-19) | 0.88(t, J=6.7Hz, 3H), 1.10–1.80(m, 32H), 2.45–3.00(m, 7H), 3.30–3.90(m, 7H). | 3420, 2932, 2860, 1470, 1110. | 1-Bromohexadecane | 80% Ethanol sol. of pyrrolidine |

*Indicating $^1$H-NMR (CDCl$_3$, δ) unless expressly noted.

Synthesis Example 20
Synthesis of Compound (1a-20) and Compound (1b-20):
(1) Synthesis of 12-methoxy-1-methanesulfonyloxyoctadecane:

A 50-ml eggplant type flask was charged with 12-methoxyoctadecanol (5.00 g, 16.6 mmol), triethylamine (2.03 g, 20.0 mmol) and tetrahydrofuran (10 g) in a nitrogen atmosphere, to which methanesulfonyl chloride (2.29 g, 20.0 mmol) was added with stirring. After the resultant mixture was stirred for 14 hours, water was added to conduct extraction with chloroform. After the resultant organic layer was washed with saturated saline, dried over anhydrous magnesium sulfate and then filtered, the resultant filtrate was concentrated under reduced pressure. The resultant residue was then purified by column chromatography on silica gel to obtain the title compound (5.15 g, yield: 82%). Colorless oil.
$^1$H-NMR (CDCl$_3$, δ):
0.89(t,J=6.7Hz,3H), 3.01(s,3H), 3.05–3.20(m,1H), 3.34(s,3H), 4.24(t,J=6.7Hz,2H). IR (cm$^{-1}$): 2932, 2860, 1468, 1360, 1176, 1098, 956.

(2) Synthesis of a mixture of Compound (1a-20) and Compound (1b-20):

The title compound was obtained by using the methanesulfonyl derivative (12-methoxy-1-methanesulfonyloxyoctadecane) in place of the alkyl halide in Synthesis Example 1.

Synthesis Examples 21 to 26

Compounds of the present invention shown in Table 11 were synthesized by respectively using methanesulfonyl derivatives synthesized from their corresponding alcohols in the same manner as in Synthesis Example 20 and their corresponding amines shown in Table 11. Incidentally, the compound of Synthesis Example 20 is also shown in Table 11.

TABLE 11

| Syn. Ex | Invention compound | NMR* | IR (cm$^{-1}$) | Methanesulfonyl derivative | Amine |
|---|---|---|---|---|---|
| 20 | Mixture of (1a-20) and (1b-20) | 0.88(t, J=6.7Hz, 3H), 1.10–1.68(m, 30H), 2.40(s, 6H), 2.42–2.80(m, 1H), 3.00–3.88(m, 13H). | 3444, 2932, 2860, 1462, 1098. | 12-Methoxy-1-methanesulfonyl-oxyoctadecane | 40% Aqueous sol. of dimethylamine |
| 21 | Mixture of (1a-21) and (1b-21) | 0.80(s, 9H), 0.84(d, J=6.7Hz, 3H), 1.18–1.72(m, 21H), 2.40(s, 3H), 2.41(s, 3H), 2.45–2.80(m, 1H), 3.32–3.88(m, 12H). | 3368, 2936, 2860, 1470, 1118. | 9-(5,5,3-trimethyl-hexyloxy)-1-methanesulfonyloxy-nonane | 40% Aqueous sol. of dimethylamine |
| 22 | Mixture of (1a-22) and (1b-22) | 0.80–1.00(m, 6H), 1.15–1.70(m, 23H), 2.35–2.82(m, 9H), 3.20–3.90(m, 11H). | 3424, 2932, 2864, 1464, 1116. | 9-(2-ethyl-hexyloxy)-1-methanesulfonyloxy-nonane | 40% Aqueous sol. of dimethylamine |
| 23 | Mixture of (1a-23) and (1b-23) | 0.80–0.95(m, 6H), 1.05–1.80(m, 21H), 2.48(s, 3H), 2.50(s, 3H), 2.52–3.90(m, 14H). | 3368, 2936, 2860, 1470, 1118. | 9-(2-methyl-hexyloxy)-1-methanesulfonyloxy-nonane | 40% Aqueous sol. of dimethylamine |
| 24 | Mixture of (1a-24) and (1b-24) | 0.88(t, J=6.7Hz, 3H), 1.08–1.68(m, 30H), 2.43(s, 3H), 2.45–2.80(m, 4H), 3.02–3.18(m, 1H), 3.30(s, 3H), 3.35–3.85(m, 7H). | 3348, 2932, 2860, 1468, 1100. | 12-Methoxy-1-methanesulfonyl-oxyoctadecane | 40% Aqueous sol. of methylamine |
| 25 | Mixture of (1a-25) and (1b-25) | 0.85(s, 9H), 0.90(d, J=6.7Hz, 3H), 1.15–1.68(m, 19H), 2.42(s, 3H), 2.46–2.72(m, 1H), 3.18(brs, 3H), 3.30–3.80(m, 11H). | | 9-(5,5,3-trimethyl-hexyloxy)-1-methanesulfonyloxy-nonane | 40% Aqueous sol. of methylamine |
| 26 | Mixture of (1a-26) and (1b-26) | 0.75–0.95(m, 6H), 1.12–1.65(m, 23H), 2.42(s, 3H), 2.45–2.75(m, 4H, | 3360, 2932, 2864, 1466, 1108. | 9-(2-ethyl-hexyloxy)-1- | 40% Aqueous sol. of methylamine |

TABLE 11-continued

| Syn. | | Invention compound | | Methanesulfonyl | |
|---|---|---|---|---|---|
| Ex | Invention compound | NMR* | IR (cm$^{-1}$) | derivative | Amine |
| | | 3.18–3.85(m, 11H). | | methanesulfonyloxy-nonane | |

*Indicating $^1$H-NMR (CDCl$_3$, δ) unless expressly noted.

Synthesis Example 27
Synthesis of a mixture of Compound (1a-27) and Compound (1b-27):

A 50-ml eggplant type flask was charged with glycine (0.53 g, 7.0 mmol), potassium hydroxide (0.39 g, 7.0 mmol) and t-butanol (5 g) in a nitrogen atmosphere, and the temperature of the contents was raised to reflux. After 2,3-epoxy-4-tridecyloxy-1-butanol (0.20 g, 0.7 mmol) was added, and the resultant mixture was stirred for 30 hours under the same conditions, the mixture was cooled to room temperature. After water was added and the pH of the reaction mixture was adjusted to 4 with 6N hydrochloric acid, extraction was conducted with chloroform-methanol. The resultant organic layer was dried over anhydrous magnesium sulfate, filtered, concentrated under reduced pressure and then purified by column chromatography to obtain the title compound (0.46 g, yield: 63%).

$^1$H-NMR (CDCl$_3$, δ):
0.90(t,J=6.7Hz,3H), 1.15–1.68(m,22H), 3.30–4.26(m, 13H). IR (cm$^{-1}$):
3280, 2928, 2860, 1730, 1470, 1398, 1116.

Synthesis Example 28
Synthesis of a mixture of Compound (1a-28) and Compound (1b-28):

A mixture of Compound (1a-28) and Compound (1b-28) was synthesized in accordance with the same technique as in Synthesis Example 27 except that glycine was changed to guanidine hydrochloride.

$^1$H-NMR (CDCl$_3$, δ):
0.90(t,J=6.7Hz,3H), 1.09–1.75(m,22H), 3.22–4.88(m, 10H), 6.68–7.55(m,4H). IR (cm$^{-1}$):
3364, 2928, 2860, 1666, 1468, 1112.

Synthesis Example 29
Synthesis of a mixture of Compound (1a-29) and Compound (1b-29):

A 10-ml eggplant type flask was charged with a mixture (0.20 g, 0.60 mmol) of Compound (1a-1) and Compound (1b-1), methylene chloride (1 ml) and 70% m-chloroperbenzoic acid (0.18 g, 0.72 mmol) in a nitrogen atmosphere, and the contents were stirred for about 10 minutes. The reaction mixture was then concentrated under reduced pressure and purified by column chromatography on silica gel to obtain the title compound (0.14 g, yield: 68%). MS (M+H)$^+$348. $^1$H-NMR (CDCl$_3$, δ):
0.88(t,J=6.7Hz,3H), 1.10–1.65(m,22H), 3.08–4.05(m, 15H), 4.20–4.52(m,1H). $^{13}$C-NMR:
14.1, 22.6, 26.0, 29.3–29.6, 31.9, 56.0, 59.0, 59.6, 68.4, 72.0, 73.5, 80.9. IR (cm$^{-1}$):
3212, 2928, 2856, 1472, 1134.

Synthesis Example 30
Synthesis of a mixture of Compound (1a-30) and Compound (1b-30):

A 10-ml eggplant type flask was charged with a mixture (0.20 g, 0.63 mmol) of Compound (1a-7) and Compound (1b-7) and toluene (1 ml) in a nitrogen atmosphere. After 60% sodium hydride (55 mg, 1.38 mmol) was charged while stirring at room temperature, dimethyl carbonate (56 mg, 0.62 mmol) was added, and the contents were stirred at 60° C. for 3 hours. After the reaction mixture was cooled to room temperature, water was added to conduct extraction with ethyl acetate. The resultant organic layer was dried over anhydrous magnesium sulfate, filtered, concentrated under reduced pressure and then purified by column chromatography on silica gel to obtain the title compound (0.16 g, yield: 72%). $^1$H-NMR (CDCl$_3$, δ):
0.80–0.98(m,3H), 1.20–1.78(m,22H), 2.55(brs,1H), 2.88 (s,3H), 3.36–3.95(m,7H), 4.25–4.54(m,1H). IR:
3436, 2928, 1748, 1724, 1474, 1418, 1134, 1106.

Synthesis Example 31
Synthesis of a mixture of Compound (1a-31) and Compound (1b-31):

A 10-ml eggplant type flask was charged with a mixture (0.20 g, 0.63 mmol) of Compound (1a-7) and Compound (1b-7) and tetrahydrofuran (1 ml) in a nitrogen atmosphere. While stirring at room temperature, acetic anhydride (76 mg, 0.74 mmol) was added, and the contents were stirred for 3 hours under the same conditions. The reaction mixture was concentrated under reduced pressure and then purified by column chromatography on silica gel to obtain the title compound (0.15 g, yield: 68%).

$^1$H-NMR (CDCl$_3$, δ):
0.88(t,J=6.7Hz,3H), 1.15–1.65(m,22H), 1.90(brs,2H), 2.14(s,3H), 3.10(s,3H), 3.20–4.15(m,7H), 4.35–4.52 (m,1H). IR (cm$^{-1}$)
3376, 2924, 2856, 1622, 1470, 1410, 1114, 1036.

Synthesis Example 32
Synthesis of a mixture of Compound (1a-32) and Compound (1b-32):

A 300-ml eggplant type flask was charged with a mixture (10.0 g, 30.2 mmol) of Compound (1a-8) and Compound (1b-8) and ethanol (50 ml) in a nitrogen atmosphere, and succinic acid (1.78 g, 15.1 mmol) was added with stirring. After the contents were stirred for 30 minutes, the reaction mixture was concentrated under reduced pressure to obtain the title compound (11.7 g). Colorless solid.

$^1$H-NMR (D$_2$O, δ):
0.75–0.98(m,3H), 1.05–1.80(m,24H), 2.38(s,2H), 2.75(s, 3H), 3.05–4.10(m,8H). IR (CDCl$_3$):
3380, 2928, 2856, 1572, 1470, 1416, 1126.

Synthesis Example 33
Synthesis of a mixture of Compound (1a-33) and Compound (1b-33):

An eggplant type flask was charged with the mixture (0.10 g, 0.30 mmol) of Compound (1a-1) and Compound (1b-1) obtained in Synthesis Example 1, THF (1 ml), 85% phosphoric acid (35 mg, 1 eq.) and diphosphorus pentaoxide (75 mg, 1.8 eq.), and the contents were heated under reflux for 2 hours. After the reaction mixture was allowed to cool to room temperature, water was added to conduct extraction with a mixed solvent of n-hexane and 2-propanol. The resultant organic layer was dried over anhydrous magnesium sulfate, filtered and then concentrated under reduced pressure to obtain the title compound (52 mg, yield: 42%).

$^1$H-NMR (CDCl$_3$, δ):

0.80–0.95(m,3H), 1.02–1.80(m,22H), 2.64–4.48(m,15H), 7.72(brs,2H). IR (cm$^{-1}$):

3404, 2932, 2860, 1470, 1122, 1012.

Synthesis Example 34

Synthesis of a mixture of Compound (1a-34) and Compound (1b-34):

An autoclave was charged with the mixture (0.50 g, 1.27 mmol) of Compound (1a-1) and Compound (1b-1) obtained in Synthesis Example 1, palladium on activated carbon (10%, 25 mg) and ethanol (2 ml) to conduct hydrogenolysis at 80° C. for 24 hours under a hydrogen pressure of 100 kg/cm$^2$. After the pressure of the autoclave was reduced back to normal pressure, the reaction mixture was filtered and concentrated under reduced pressure. The resultant residue was purified by column chromatography on silica gel to obtain the title compound (0.22 g, yield: 56%).

$^1$H-NMR (CDCl$_3$, δ):

0.80–0.98(m,3H), 1.05–1.75(m,22H), 2.25(brs,4H), 2.44–2.92(m,1H), 3.30–3.95(m,7H). IR (cm$^{-1}$):

3384, 2928, 2860, 1468, 1110.

Test Example 1

Figure 2:
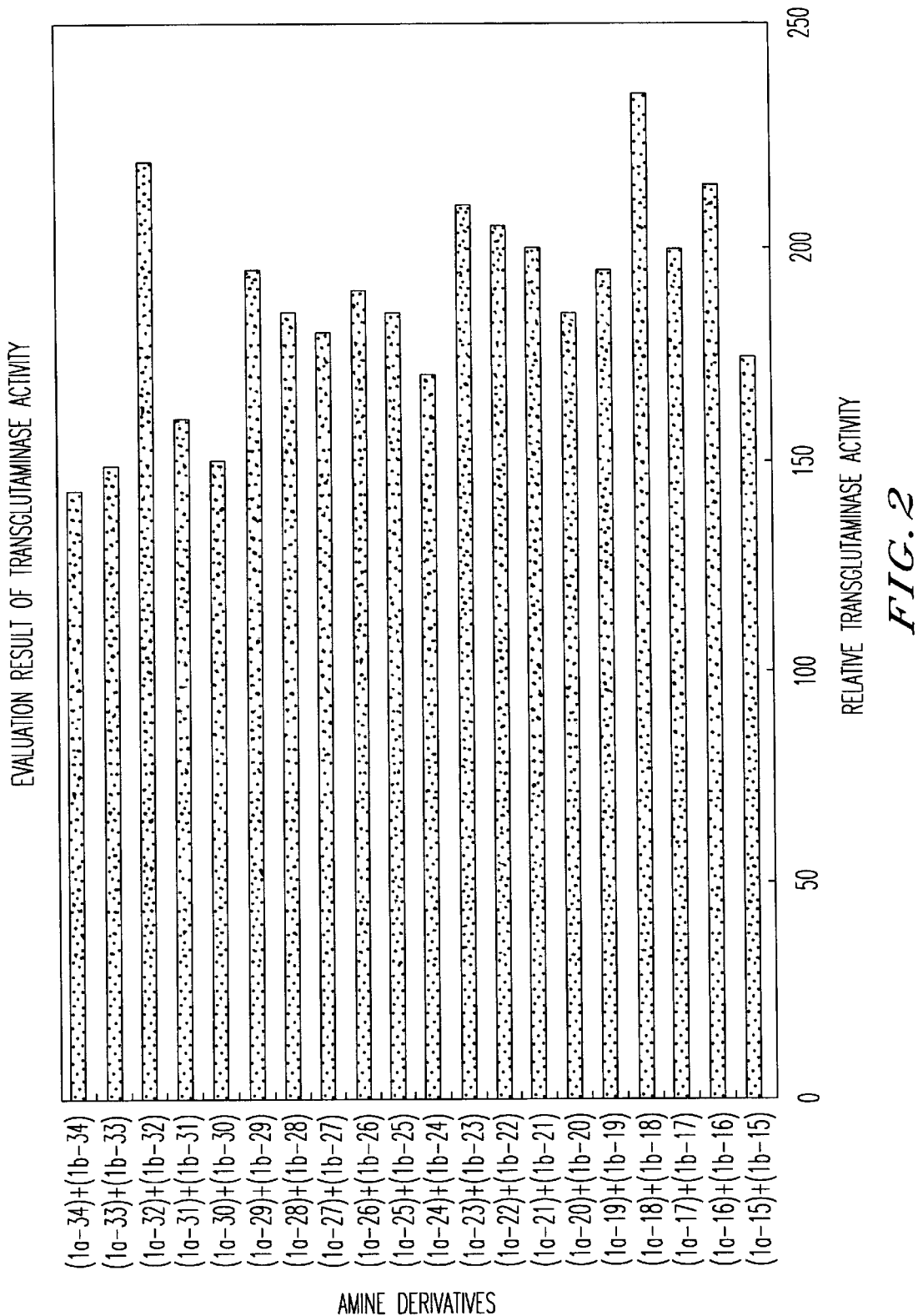

Investigation as to transglutaminase activity of epidermic keratinocyte:

Epidermic keratinocytes cultured in a vegetative state in a petri dish were used. A medium in each well was removed by suction, and K-GM (10 ml), to which no pituitary extract was added, was added to conduct medium exchange. Thereafter, each amine derivative (10 μl) obtained above was added. After 24 hours, each well was washed 3 times with PBS(–), and cells were than separated and recovered by a rubber policeman. The resultant cell suspension was centrifuged for 10 minutes at 2,500 rlmin to recover sediment. Buffer (a) [10 mmol/L Tris-HCl buffer, 10 mmol/L DTT, 0.5 mmol/L EDTA; pH 7.4; 200 ul] was added to the sediment to conduct sonication with ultrasonic wave for 1 minute twice. The resultant suspension was supercentrifuged for 30 minutes at 25,000 r/min to obtain a supernatant. After this supernatant was divided into equal portions, a reactive solution [solution obtained by mixing 300 mmol/L Tris-HCl buffer, pH 8.1; 60 mmol/L CaCl$_2$ (100 μl); 30 mmol/L DTT (100 μl); distilled water (100 μl) containing dimethylcasein (540 μg); 12 mmol/L putrescine (50 μl); 2.5 μCi [$^{14}$C] putrescine (50 μl); and distilled water (100 μl)] was added to each portion to conduct incubation at 37° C. for 1 hour. After 10% trichloroacetic acid was then added to leave the resultant mixture at rest for 30 minutes, sediment (200 μl) was recovered through a nitrocellulose membrane having a pore size of 0.45 μm. After this membrane was washed with ice-cooled 5% trichloroacetic acid (15 ml) [containing 1% putrescine], radioactivity on the membrane was counted by a liquid scintillation counter. Transglutaminase activities when the respective amine derivatives (1) were added are illustrated in terms of a proportion regarding the activity of a control as 100% in FIGS. 1 and 2. As apparent from the results, the amine derivatives (1) according to the present invention have a transglutaminase activating effect.

Test Example 2

Effect of accelerating production of cathepsin D on cultured epidermic cell:

Normal human epidermic cells (Kyokuto Seiyaku) were respectively treated with amine derivatives (1) shown in Table 12 to detect cathepsin D, which is a protease derived from lamellar granules isolated in a medium, by the Western blot technique, and the intensity of a band thereof was compared with a control (control with no amine derivative added). The results are shown in Table 12 as an average value of 3 runs.

TABLE 12

| Substance tested | Relative effect of accelerating production of cathepsin D |
| --- | --- |
| Control | 1 |
| (1a – 1) | 6 |
| (1b – 1) | 8 |
| (1a – 1) + (1b – 1) | 3 |
| (1a – 2) + (1b – 2) | 3 |
| (1a – 4) + (1b – 4) | 2 |
| (1a – 5) + (1b – 5) | 2 |
| (1a – 6) + (1b – 6) | 3 |
| (1a – 7) | 6 |
| (1b – 7) | 10 |
| (1a – 7) + (1b – 7) | 8 |
| (1a – 8) + (1b – 1) | 8 |
| (1a – 9) + (1b – 9) | 7 |
| (1a – 11) + (1b – 11) | 6 |
| (1a – 13) + (1b – 13) | 14 |
| (1a – 14) + (1b – 14) | 6 |
| (1a – 14) | 6 |
| (1b – 14) | 6 |
| (1a – 16) + (1b – 16) | 12 |
| (1a – 18) + (1b – 18) | 12 |
| (1a – 21) + (1b – 21) | 5 |
| (1a – 22) + (1b – 22) | 5 |
| (1a – 23) + (1b – 23) | 5 |
| (1a – 27) + (1b – 27) | 7 |
| (1a – 28) + (1b – 28) | 7 |
| (1a – 29) + (1b – 29) | 8 |
| (1a – 32) + (1b – 32) | 6 |

Test Example 3

Figure 3:
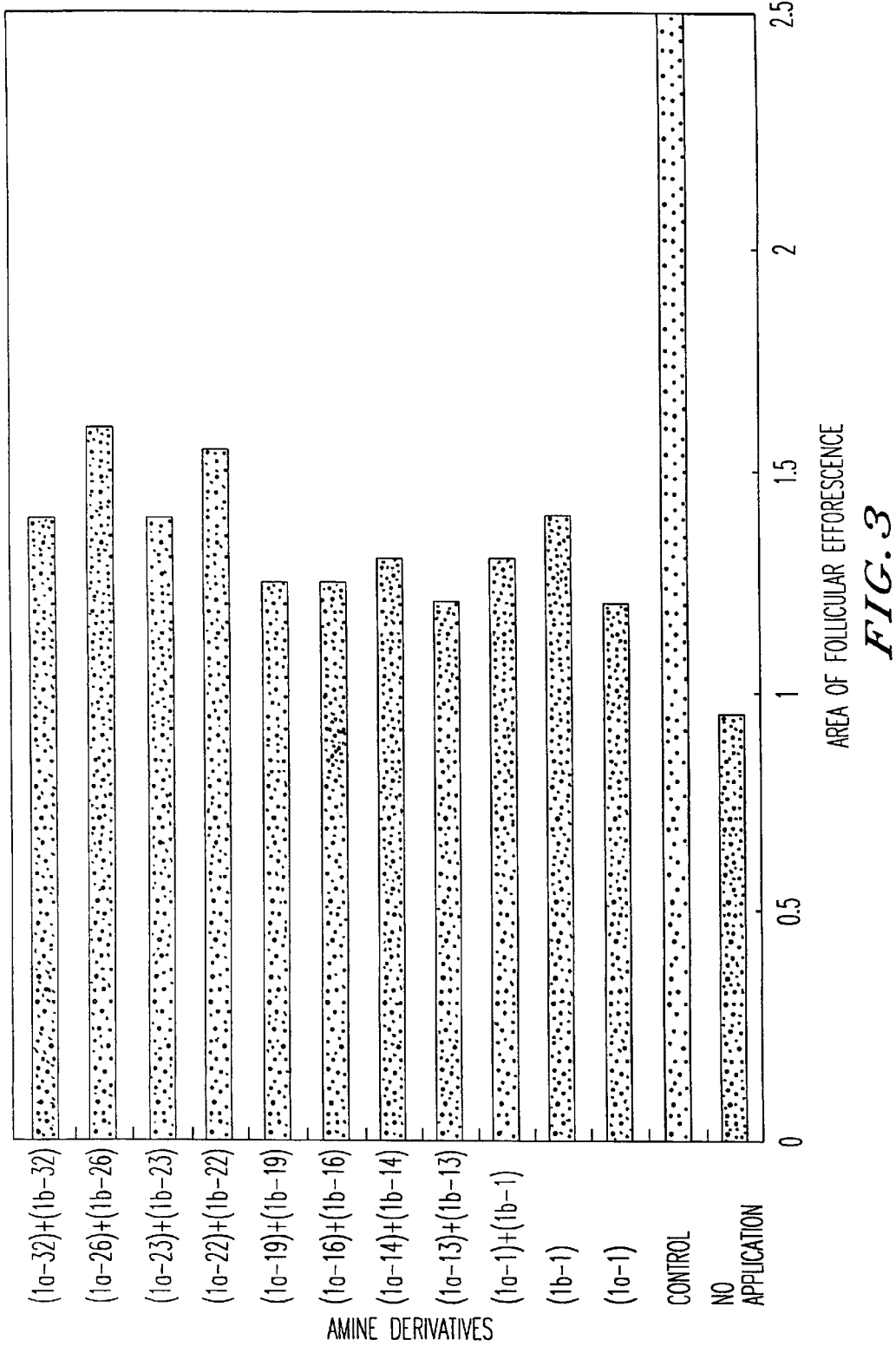
FIG. 3 illustrates areas of follicular efflorescences inhibited by the amine derivatives (1) according to the present invention.

Investigation as to effect of amine derivatives (1) on experimental formation of comedo by tetradecane:

Auriclar inner skins of New Zealand white rabbits (male, weight: 2.0 to 2.5 kg) were used. Each of 50% Tetradecane (squalane solution) and 50% tetradecane (squalane solution) containing each amine derivative (0.01%) was applied in an amount of 0.3 ml to the skin continuously for 2 weeks once a day. After 2 weeks, an area of a follicular efflorescence (experimental comedo) was measured by means of a surface microscope. As controls, were used a case (no application) where no application was conducted and a case (control) where 50% tetradecane containing no amine derivative (1) was only applied. The results are shown in FIG. 3. It is understood that the amine derivatives (1) inhibit the formation of the experimental comedo.

Test Example 4

Investigation as to effect of amine derivatives (1) on wrinkles formed on hairless mice by exposure to UVB:

Hairless mice (HR/ICR, aged 9 weeks at the beginning of the experiment) were exposed to UVB 3 times a week by using 6 Toshiba healthy lamps, 20SE. The amount of energy was measured by means of a UV-Radiometer, UVR-305/365D manufactured by TOKYO OPTICAL K.K. The dose upon one exposure was determined to be 1 MED or less, i.e., 65 mJ in an amount of energy of 0.28 mW/cm$^2$. The exposure was effected for 20 weeks. After confirming that the hairless mice had got wrinkles at their backs, they were divided into groups each consisting of 8 mice. Ethanol solutions separately containing amine derivatives (1) in an amount of 0.025% were applied 5 times a week to their corresponding groups of mice over 6 weeks in a dose of 80 μl. As a control, ethanol containing no amine derivative was applied like the samples. After completion of the application, the degree of wrinkles was visually observed to evaluate the samples in accordance with the following standard (wrinkle index). The results are shown in Table 13.

(Wrinkle index)

1: Wrinkles were completely removed or smoothed;
2: Wrinkles were scarcely observed;
3: Wrinkles were somewhat observed;
4: Wrinkles were observed to a great extent.

In order to further analyze the particulars of wrinkles, skin replicas of the size of 1 cm in diameter were gathered from 3 portions of each of the mice using a Hydrophilic Exaflex hydrophilic vinylsilicone impression material. Each of these replicas was held horizontally and illuminated at an angle of 30 degrees from the horizontal direction, thereby finding a proportion of shadows of the wrinkles as an area percent by means of an image analyzer. The results are shown in Table 13.

TABLE 13

| Amine derivative | Wrinkle index | Area percent of wrinkles (%) |
| --- | --- | --- |
| Control | 3.85 ± 0.10 | 6.52 ± 0.50 |
| (1a – 1) | 2.89 ± 0.12 | 2.95 ± 0.22 |
| Mixture of (1a – 1) and (1b – 1) | 3.01 ± 0.20 | 3.10 ± 0.19 |
| Mixture of (1a – 7) and (1b – 7) | 2.90 ± 0.12 | 3.05 ± 0.15 |
| Mixture of (1a – 19) and (1b – 19) | 2.95 ± 0.15 | 3.00 ± 0.12 |

It is understood that the amine derivatives (1) according to the present invention can improve wrinkles.

Example 1

Preparation of W/O cream

An external skin care composition having the following formulation was prepared in accordance with a method known per se in the art.

| | | (%) |
| --- | --- | --- |
| (1) | Mixture of Amine Derivatives (1a – 19) and (1b – 19) | 0.1 |
| (2) | Cholesterol | 0.5 |
| (3) | Cholesteryl isostearate | 1.0 |
| (4) | Polyether-modified silicone | 1.5 |
| (5) | Cyclic silicone | 20.0 |
| (6) | Methylphenylpolysiloxane | 2.0 |
| (7) | Methylpolysiloxane | 2.0 |
| (8) | Magnesium sulfate | 0.5 |
| (9) | 55% Ethanol | 5.0 |
| (10) | Carboxymethylchithin (Chithin Liquid HV, product of Ichimar Pharcos Co., Ltd.) | 0.5 |
| (11) | Purified water | Balance |

Example 2

Preparation of ointment

An external skin care composition having the following formulation was prepared in accordance with a method known per se in the art.

| | | (%) |
| --- | --- | --- |
| (1) | Mixture of Amine Derivatives (1a – 1) and (1b – 1) | 0.05 |
| (2) | White petrolatum | Balance |
| (3) | Cholesteryl isostearate | 3.0 |
| (4) | Liquid paraffin | 10.0 |
| (5) | Isostearyl glyceryl ether | 1.0 |
| (6) | Glycerol | 10.0. |

Both external skin care compositions prepared in Examples 1 and 2 had a preventing effect on aging of the skin and an improving effect on cutaneous troubles caused by keratonosis.

INDUSTRIAL APPLICABILITY

The external skin care compositions according to the present invention have preventing effects (wrinkle preventing and improving effect, pigmentation preventing and improving effect, etc.) on aging of the skin, and improving effects (keratonosis improving effect, pimple preventing and improving effect, etc.) on cutaneous aberration caused by abnormal keratinization, and are hence useful for medicines and cosmetics.

What is claimed is:

1. An amine derivative represented by the general formula (1):

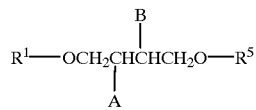

wherein

R$^1$ is a hydrocarbon group having 1 to 30 carbon atoms, which may be interrupted by an ether linkage, with the proviso that phenyl and benzyl groups are excluded;

one of A and B is

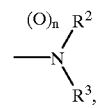

and the other of them is —OR$^4$;

R$^2$ and R$^3$ are the same or different from each other and are individually a hydrogen atom, an amidino group, an alkanoyl group or a hydrocarbon group having 1 to 20 carbon atoms, which may have 1 to 3 substituent groups selected from hydroxyl, alkoxy and carboxyl groups, or R$^2$ and R$^3$ may form a 5- or 6-membered nitrogen-containing heterocycle together with the adjacent nitrogen atom, or R$^3$ and R$^4$, or R$^3$ and R$^5$ may be bonded to each other through a carbonyl group to form an oxazolidone ring;

R$^4$ and R$^5$ are the same or different from each other and are individually a hydrogen atom or a phosphoryl group, or R$^4$ or R$^5$ may form the oxazolidone ring together with R$^3$; and n is a number of 0 or 1, or a quaternary ammonium salt or acid-addition salt thereof.

2. The compound according to claim 1, wherein R$^1$ is a linear or branched hydrocarbon group having 8 to 30 carbon atoms, which may be interrupted by an ether linkage.

3. The compound according to claim 1, wherein n is 0, and $R^4$ and $R^5$ are hydrogen atoms.

4. The compound according to claim 1, wherein n is 0, $R^2$ and $R^3$ are both methyl groups or form a 5- or 6-membered nitrogen-containing heterocycle together with the adjacent nitrogen atom, and $R^4$ and $R^5$ are hydrogen atoms.

5. The compound according to claim 1, wherein $R^1$ is an alkyl group having 8 to 30 carbon atom or an alkoxyalkyl group having 8 to 30 carbon atoms.

6. An external skin care composition comprising the compound according to any one of claims 1 to 5.

7. The compound according to claim 2, wherein n is 0, and $R^4$ and $R^5$ are hydrogen atoms.

8. The compound according to claim 2, wherein n is 0, $R^2$ and $R^3$ are both methyl groups or form a 5- or 6-membered nitrogen-containing heterocycle together with the adjacent nitrogen atom, and $R^4$ and $R^5$ are hydrogen atoms.

9. The compound according to claim 2, wherein $R^1$ is an alkyl group having 8 to 30 carbon atom or an alkoxyalkyl group having 8 to 30 carbon atoms.

10. The compound according to claim 3, wherein $R^1$ is an alkyl group having 8 to 30 carbon atom or an alkoxyalkyl group having 8 to 30 carbon atoms.

11. The compound according to claim 4, wherein $R^1$ is an alkyl group having 8 to 30 carbon atom or an alkoxyalkyl group having 8 to 30 carbon atoms.

12. The compound according to claim 7, wherein $R^1$ is an alkyl group having 8 to 30 carbon atom or an alkoxyalkyl group having 8 to 30 carbon atoms.

13. The compound according to claim 8, wherein $R^1$ is an alkyl group having 8 to 30 carbon atom or an alkoxyalkyl group having 8 to 30 carbon atoms.

* * * * *